(12) United States Patent
Sundling

(10) Patent No.: US 10,974,006 B2
(45) Date of Patent: Apr. 13, 2021

(54) FACE MASK ARRANGEMENT, SYSTEM CONTAINING IT AND USE THEREOF FOR ADMINISTRATION

(71) Applicant: MedClair AB, Borlänge (SE)

(72) Inventor: Jerker Sundling, Borlänge (SE)

(73) Assignee: Medclair AB, Borlänge (SE)

( * ) Notice: Subject to any disclaimer, the term of this patent is extended or adjusted under 35 U.S.C. 154(b) by 1650 days.

(21) Appl. No.: 14/431,876

(22) PCT Filed: Oct. 3, 2013

(86) PCT No.: PCT/SE2013/051162
§ 371 (c)(1),
(2) Date: Mar. 27, 2015

(87) PCT Pub. No.: WO2014/055026
PCT Pub. Date: Apr. 10, 2014

(65) Prior Publication Data
US 2015/0246197 A1 Sep. 3, 2015

(30) Foreign Application Priority Data
Oct. 5, 2012 (SE) .................... 1251126-7

(51) Int. Cl.
*A61M 16/06* (2006.01)
*A61M 16/12* (2006.01)
(Continued)

(52) U.S. Cl.
CPC ........ *A61M 16/06* (2013.01); *A61M 16/0003* (2014.02); *A61M 16/009* (2013.01);
(Continued)

(58) Field of Classification Search
CPC .. A61M 16/06; A61M 16/104; A61M 16/009; A61M 16/10; A61M 2202/0283; A61M 16/12; A61M 16/20; Y02C 20/10
(Continued)

(56) References Cited

U.S. PATENT DOCUMENTS

| 4,538,605 A | 9/1985 | Gedeon et al. |
| 6,024,087 A * | 2/2000 | Kersey .................. A61M 16/12 128/203.12 |

(Continued)

FOREIGN PATENT DOCUMENTS

| DE | 43 12 431 C1 | 4/1994 |
| WO | WO 2011/038303 A1 | 3/2011 |
| WO | WO 2011/075033 A1 | 6/2011 |

OTHER PUBLICATIONS

"Development and Design of a Patient Controlled, Electric Regulated Gas Valve for Nitrous Oxide/Oxygen and Oxygen/Air", Karolinska Institute, Stockholm 2005, pp. 1-21.

*Primary Examiner* — Victoria Murphy
(74) *Attorney, Agent, or Firm* — Blank Rome LLP

(57) ABSTRACT

The invention relates to a face mask arrangement for alternately administering a gas I containing nitrous oxide and a gas II devoid of nitrous oxide to a patient, comprising a face mask, two inlet flow lines I and II for gas I and a gas II, respectively, which flow lines end in a breathing interface, and an outlet flow line for evacuation of exhaled gas. The two inlet flow lines merge into a common inlet part. Each of the inlet flow lines I and II comprises an inlet valve I and II, each of which is capable of opening in response to inhalation and of closing in response to exhalation. The arrangement comprises a switching means enabling switching between inhalation through inlet flow line I and inlet flow line II depending on the patient's immediate need of gas I or gas II. The invention relates also to a system comprises the face
(Continued)

mask arrangement and an apparatus for collecting inhalation air from patients inhaling gas containing nitrous oxide and to the use of the face mask arrangement for administration of nitrous oxide to a patient via inhalation and collecting nitrous oxide from exhaled air of a patient during the administration.

15 Claims, 5 Drawing Sheets

(51) Int. Cl.
    *A61M 16/10*      (2006.01)
    *A61M 16/00*      (2006.01)
    *B01D 53/86*      (2006.01)
    *B01D 53/04*      (2006.01)
    *A61M 16/20*      (2006.01)
    *A61M 16/01*      (2006.01)

(52) U.S. Cl.
    CPC .... *A61M 16/0051* (2013.01); *A61M 16/0066* (2013.01); *A61M 16/10* (2013.01); *A61M 16/104* (2013.01); *A61M 16/1075* (2013.01); *A61M 16/122* (2014.02); *A61M 16/20* (2013.01); *B01D 53/04* (2013.01); *B01D 53/8631* (2013.01); *A61M 16/0093* (2014.02); *A61M 16/01* (2013.01); *A61M 16/202* (2014.02); *A61M 16/208* (2013.01); *A61M 2202/0283* (2013.01); *A61M 2205/18* (2013.01); *A61M 2205/3368* (2013.01); *A61M 2205/581* (2013.01); *A61M 2205/583* (2013.01); *A61M 2230/04* (2013.01); *A61M 2230/30* (2013.01); *A61M 2230/40* (2013.01); *A61M 2230/437* (2013.01); *B01D 2257/404* (2013.01); *B01D 2258/06* (2013.01); *B01D 2259/4009* (2013.01); *B01D 2259/4533* (2013.01); *B01D 2259/4541* (2013.01); *Y02C 20/10* (2013.01)

(58) Field of Classification Search
    USPC ........................................................ 137/112
    See application file for complete search history.

(56) References Cited

U.S. PATENT DOCUMENTS

| | | | |
|---|---|---|---|
| 6,076,392 A * | 6/2000 | Drzewiecki | A61M 16/0051 |
| | | | 73/23.2 |
| 7,235,222 B2 | 6/2007 | Hotta et al. | |
| 9,789,273 B2 * | 10/2017 | Lucci | A61M 16/06 |
| 2002/0069878 A1 * | 6/2002 | Lurie | A61H 31/005 |
| | | | 128/204.18 |
| 2004/0034287 A1 * | 2/2004 | Hickle | A61B 5/1106 |
| | | | 600/300 |
| 2004/0168686 A1 * | 9/2004 | Krebs | A61M 16/009 |
| | | | 128/203.12 |
| 2009/0223567 A1 | 9/2009 | Ahearn et al. | |

\* cited by examiner

FACE MASK ARRANGEMENT, SYSTEM CONTAINING IT AND USE THEREOF FOR ADMINISTRATION

FIELD OF THE INVENTION

The invention relates to a face mask arrangement, a system containing the arrangement for a) alternately administration of gas containing nitrous oxide and a gas containing oxygen but no nitrous oxide to a patent via inhalation, and b) collecting exhalation air during the administration. The invention also relates to a system containing the arrangement and to use of the face mask arrangement for administration of gas containing nitrous oxide and a gas containing oxygen but no nitrous oxide to a patent via inhalation.

TECHNICAL BACKGROUND

Nitrous oxide is an air pollutant which is considered at least 300 times more effective than carbon dioxide as a "green house gas". It is also considered hazardous for people exposed to it during work (e.g. doctors, dentists, nurses etc). Occupational health limits have been set to 25 ppm in many countries.

Within health care units, nitrous oxide is used within surgery, dental care, maternity care during delivery etc. due to its anaesthetic and analgesic effects on patients. The typical patient is allowed to inhale a gas mixture (=inhalation air) in which the main components are nitrous oxide, typically in concentrations of $\geq 10\%$, such as $\geq 20\%$ and/or $\leq 80\%$, such as $\leq 70\%$ (v/v) and oxygen. When an enhanced anaesthetic effect is desired, the mixture typically also contains a gaseous anaesthetic agent other than nitrous oxide. As a rule this agent is present in concentrations of $\leq 10\%$ with typically levels being in the range of 0.25-3%, such as 0.5-2% (v/v). Suitable anaesthetic agents have often been selected amongst volatile halo-containing organic compounds.

Gas containing oxygen but no nitrous oxide means in particular oxygen gas, ambient atmosphere, air from a pressurized storage tank, physiologically acceptable mixtures of oxygen gas with gases other than nitrous oxide etc.

During health care applications, such as delivery of babies, dentists' patients etc., inhalation of a gas containing nitrous oxide is often alternated with inhalation of gas containing oxygen but no nitrous oxide. Inhalation is typically via a face mask which in some of the applications may intermittently be taken of allowing the patient to breathe ambient atmosphere. The frequency and the length of periods for a particular gas and for breathing ambient atmosphere may vary in an irregular way within a treatment, between treatments of the same kind, between patients etc.

There are several alternatives for taking care of nitrous oxide in exhalation air. Typical examples are a) catalytic decomposition, b) compression/condensation, and c) adsorption. For some years the main focus in hospitals has been on catalytically decompose nitrous oxide in highly diluted forms in a central decomposition apparatus receiving highly diluted nitrous oxide from several parts of the hospital. Typical apparatus are described in WO 2011075033 (Nordic Gas Cleaning AB), WO 20101071538 (US20110262332, Nordic Gas Cleaning AB), and WO 2002026355 (U.S. Pat. No. 7,235,222, Showa Denko KK). The decomposition efficiency has been good with more than 95% of collected nitrous oxide being decomposed to nitrogen $N_2$ and oxygen $O_2$ and with very low production of hazardous nitrogen oxides other than nitrous oxide (Ek & Tjus, *Destruction of Medical N2O in Sweden*, IVL Swedish Environmental Research Institute, and EK & Tjus, *Decreased emission of nitrous oxide from delivery wards—case study in Sweden*, Mitig. Adapt. Strateg. Glob. Change (2008) 13:809-818). More recently there has been an upcoming interest in apparatuses for close to patient use requiring decomposition of nitrous oxide in more concentrated forms. Apparatuses for this use are described in EP 2165756 (Linde AG) and international patent application PCT/SE2012/000044 (US61/469,381, Nordic Gas Cleaning AB). Apparatus for adsorption of nitrous oxide close to the patient are described in WO 2009095601, WO 2009095605 and WO 2009095611 (all of Air Liquid) and PCT/SE2012/000043 (U.S. 61/469,369, Nordic Gas cleaning).

Calculations have shown that proportionally large amounts (up to 25-35%) of the used nitrous oxide escape collection. Recognized leakage sources have been deficient collection at the patient's bedside and leaking from the central system for handling gas containing nitrous oxide. Poor collection at bedsides basically depends on a number of facts: a) the typical patient inhaling nitrous oxide is awake and normally controls the inhalation during medical care involving administration of nitrous oxide (mothers during delivery, dentists' patients etc.), b) the need for pain relief typically varies over time meaning that the need for nitrous oxide only is periodical during the treatment, c) breathing via a face mask is uncomfortable for a patient being awake etc. The general practice has been that patients are taking the face mask on and off depending on their subjective need for nitrous oxide. This means that nitrous oxide will be able to escape directly into ambient atmosphere, e.g. from the open mask or when the patient via his/her lungs ventilates nitrous oxide remaining in his blood and lungs. Leakage from a central gas handling systems has among others been attributed to difficulties with proper balancing of valves, flow velocity, decomposing efficiency, cost-effectiveness with respect to consumption of energy etc in relation to irregular and unpredictable time variations in incoming levels of nitrous oxide to be decomposed.

Thus, there is a need for systems enabling administration and collection of nitrous oxide and destruction of nitrous, as well as for improved face mask arrangements.

In the prior art face mask arrangements used for the administration of nitrous oxide have so far comprised (FIG. 1a):

a) A face mask 101 as such, i.e. the part of the arrangement covering the mouth, nose or both defining a breathing interface 102 between the mask 101 and a patient using the mask and a common space 103 or volume through which both exhalation and inhalation air have to pass.

b) One inlet flow lines I 104 for a first gas I containing nitrous oxide and one optional inlet flow line II 105 for a second gas II containing oxygen but no nitrous oxide. Both flow lines 104 and 105 are ending in the breathing interface 102. When there are two inlet flow lines they are merging into a common inlet part 106 before ending in the breathing interface 102. In other words the downstream parts of each of the two inlet flow lines coincide with each other. The two upstream parts 107 and 108 of the two flow lines 104 and 105 are thus non-coinciding. Each of the inlet flow lines comprises an inlet valve I 109 and II 110, respectively, which
  i) is capable of opening in response to inhalation and closing in response to exhalation, and ii) is placed upstream of the common inlet part 106, i.e. in the non-coinciding part 107 and 108 of the inlet flow line 104 and 105, respectively.

c) An outlet flow line 111, which is starting in the breathing interface 102 and used for evacuation of exhaled gas (exhalation air). The upstream part of this flow line 111 coincides with the downstream part of the common inlet part 106 forming a common inlet/outlet part (=common space 103) through which exhalation and inhalation air have to pass. This flow line 111 has an outlet valve 112 which i) is placed in the outlet flow line 111 at a position downstream of the common inlet/outlet part 103 (i.e. in a non-coinciding part 113 of the outlet flow line 111, and ii) is capable of opening in response to exhalation and of closing in response to inhalation.

FIG. 1b illustrates variants in which the common inlet part 106 and the common inlet/outlet part (103, =common space) fully overlap each other.

Earlier face mask arrangements for administration of nitrous oxide are illustrated in WO1982001999 (Lindkvist), WO 2007035093 (Think Global B.V.), WO 2008070918 (Dunlop) and WO 2011094018 (Nashed).

Most face masks in use nowadays are considered disturbing due to a high and irregular noise resulting from the time to time use during a medical care period.

All patent applications and issued patents cited in this specification are hereby incorporated by reference.

OBJECTS OF THE INVENTION

The main object of the invention is to provide improved face mask arrangements, systems containing a face mask as well as use of said face mask arrangement for administering and/or collecting nitrous oxide to/from a patient. This main object includes improvements in the relation to the problems indicated in the preceding paragraph:

i) Lowering the proportion of nitrous oxide leaking to ambient atmosphere when a patient is breathing (inhaling and/or exhaling) nitrous oxide.

ii) Improving patient control when and how to switch between inhaling gas containing nitrous oxide and gas containing no nitrous oxide.

iii) Improving patient control when to take off the face mask.

iv) Lowering the noise from face masks in use.

v) Lowering the energy and costs for decomposition of nitrous oxide.

Subobject (i) comprises both leakage at the face mask and in the gas transportation system between the face mask and an apparatus for removing nitrous oxide from collected inhalation air.

THE INVENTION

The invention wholly or partly meets the objects above and comprises three main aspects: 1) A face mask arrangement, 2) A system comprising a face mask arrangement and an apparatus for removing nitrous oxide exhaled by a patient, and 3) Use of the face mask arrangement for administration of nitrous oxide to a patient via inhalation and/or collecting and removing nitrous oxide from exhaled air of a patient during the administration.

DRAWINGS

The invention will be described below with reference to the accompanying drawings, on which FIG. 1a-b illustrates two variants of prior art face mask arrangements comprising one or two inlet flow lines and one outlet flow line. Each inlet flow line has an inlet which opens in response to inhalation. The outlet flow line has an outlet valve which opens in response to exhalation.

FIG. 2a-d illustrate variants of the invention in which at least one of the inlet flow lines is associated with a blocking function capable of physically blocking/unblocking an inlet flow line irrespective of inhalation or exhalation.

Figure 1A:
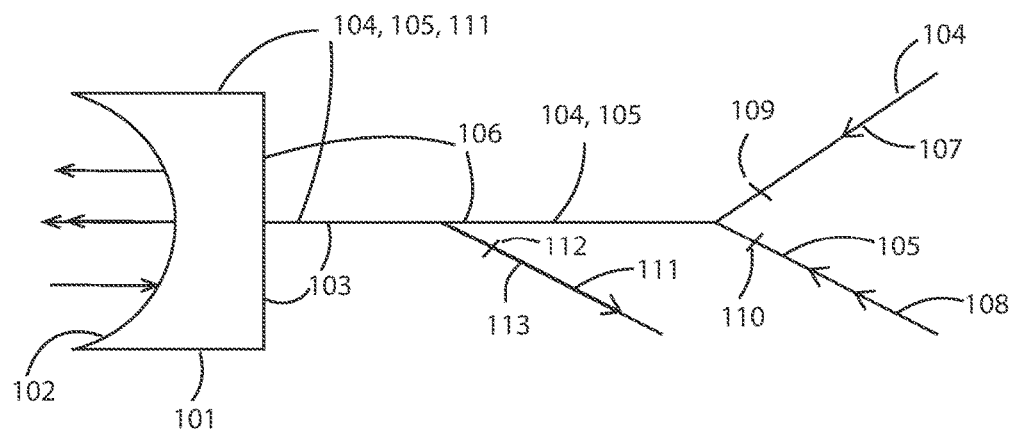
Figure 1B:
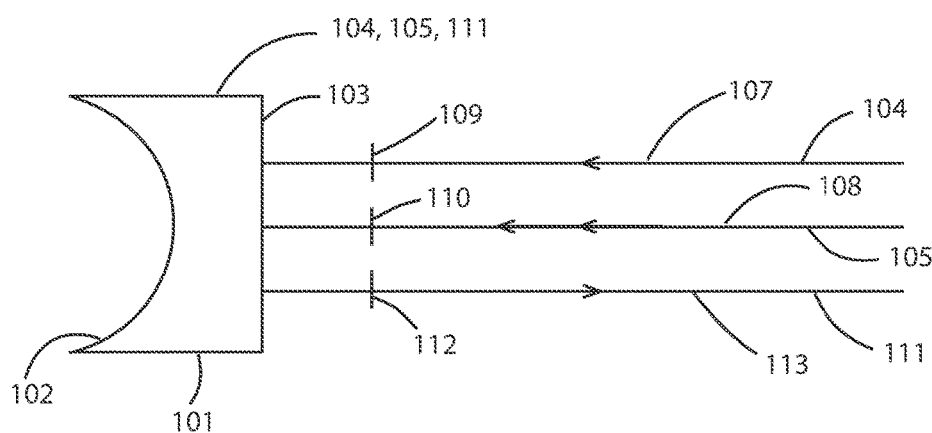

For FIGS. 1a and b the same reference numerals are used for corresponding items. For FIGS. 2a-e the general rule is that corresponding items have the same reference numeral except for corresponding items differing between the figures. The reference numerals of these latter items are ending with the letter of the figure showing the difference. The direction of exhalation flow is given with a single arrow pointing to the right. Direction of inhalation flow is given by arrows pointing to the left. A single arrow represents gas containing nitrous oxide and a double arrow represents gas devoid of nitrous oxide.

Face Mask Arrangement (1$^{st}$ Aspect of the Invention)

This aspect is an arrangement comprising:

a) a face mask 201 as such defining a breathing interface 202, b) two inlet flow lines I 204 and II 205 for a first gas I and a second gas II, respectively, as discussed above which flow lines are ending in the breathing interface 202 of the face mask 201, and c) an outlet flow line 211 which is starting in the breathing interface 202 of the face mask 201 and used for evacuation of exhaled gas (exhalation air), wherein d) the two inlet flow lines 204 and 205 are merging into a common inlet part 206 ending in the breathing interface 202, e) the downstream part of the common inlet part is coinciding with the downstream part of the outlet flow line forming a common inlet/outlet part 203, =common space, f) each of inlet flow lines I and II 204 and 205 comprises an inlet valve I and II 209 and 210, respectively, which is capable of opening in response to inhalation and of closing in response to exhalation.

The face mask arrangement also has features as described for face masks under Technical Background. The outlet flow line 211 thus has an outlet valve 212 which is placed in a part of the flow line which is not coinciding with inlet flow lines I or II (i.e. in a non-coinciding part 213 of the outlet flow line 211 and is capable of opening in response to exhalation and of closing in response to inhalation.

The characterizing feature of the 1$^{st}$ aspect is that the face mask arrangement comprises a switching means for switching between inhalation through inlet flow line I 204 and inlet flow line II 205, said switching means being configured to be activated by the patient as a response to the patient's immediate need of gas I or gas II, and that said face mask arrangement further comprises an alarm function indication when the level of nitrous oxide in exhalation air is below a predetermined value so that the face mask may be removed from the patient's face. The switching means is preferably arranged so as to allow the patient himself to exercise the actual switching. See below.

Each of the inlet valves I 209 and II 210 can be based on a flexible membrane or can be some other kind of sub-pressure sensitive valve including also valves of the demand type. The outlet valve 212 is a flexible check valve. It can be based on a) a flexible membrane or b) some other kind of over-pressure sensitive valve. Sub-pressure in the context of the invention means a pressure difference created at an inlet valve by inhaling. Over-pressure analogously means a pressure difference created at an outlet valve by exhaling.

Figure 2A:
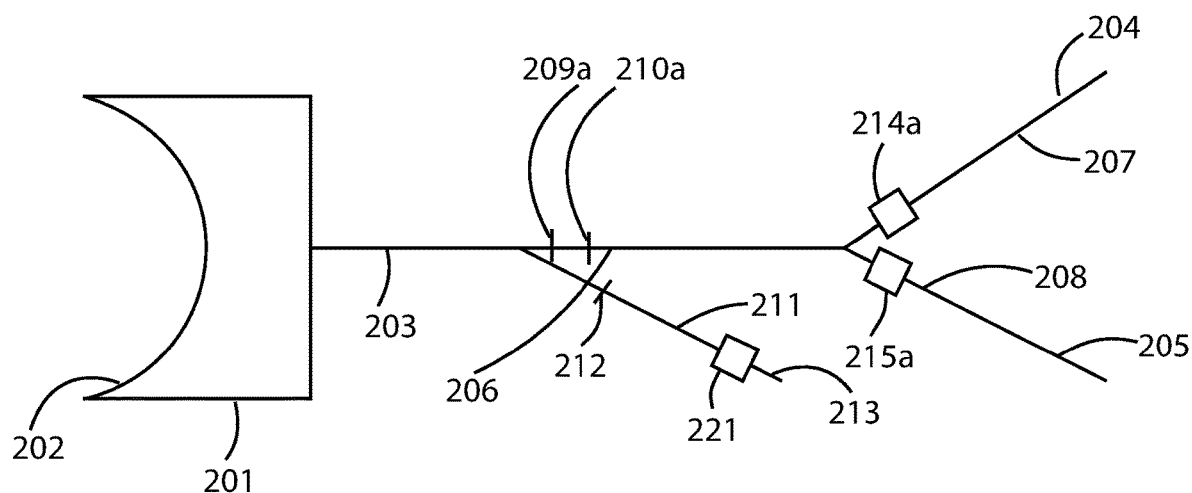
FIG. 2e illustrates a variant comprising a mixing arrangement.
FIG. 2f illustrates the mixing zone.
Figure 2B:
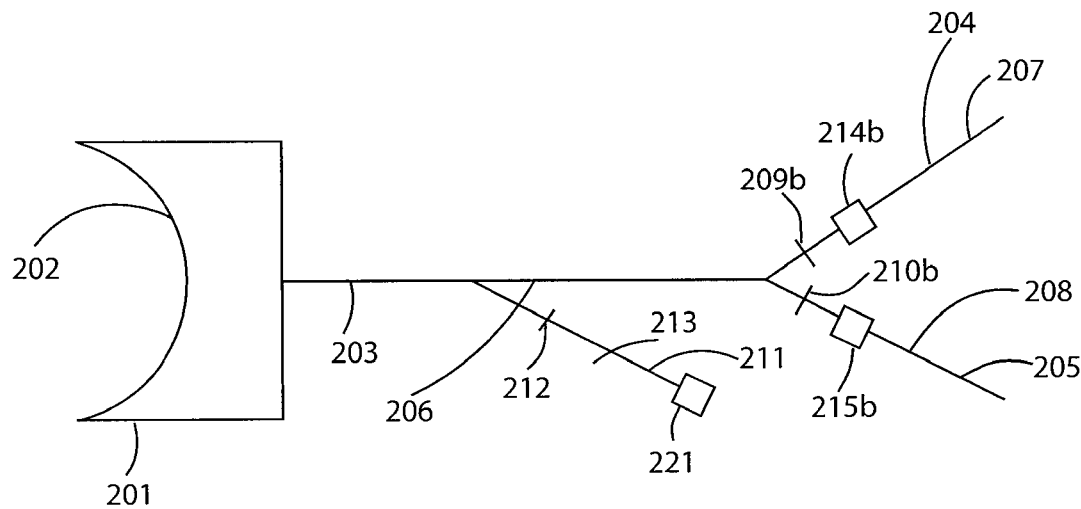
Figure 2C:
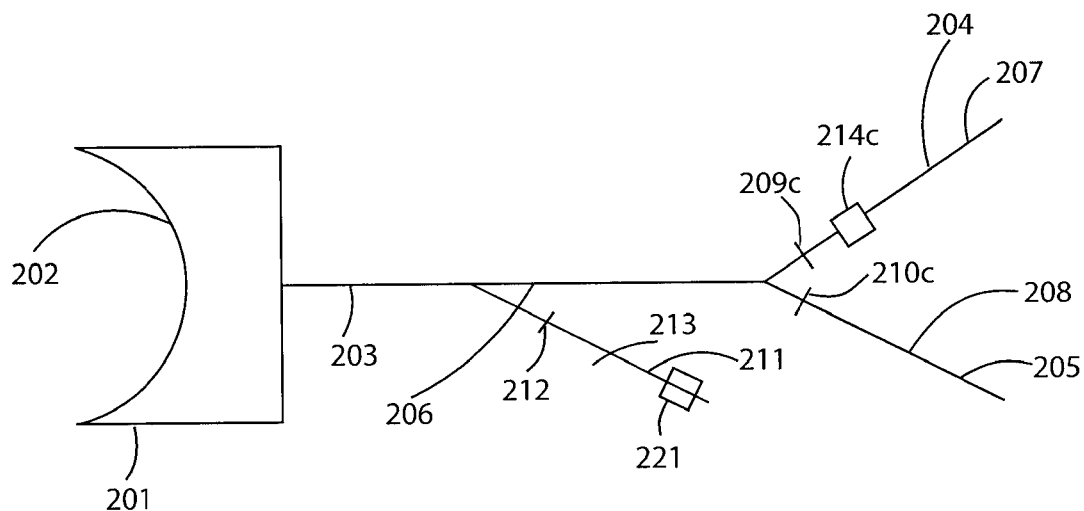
Figure 2D:
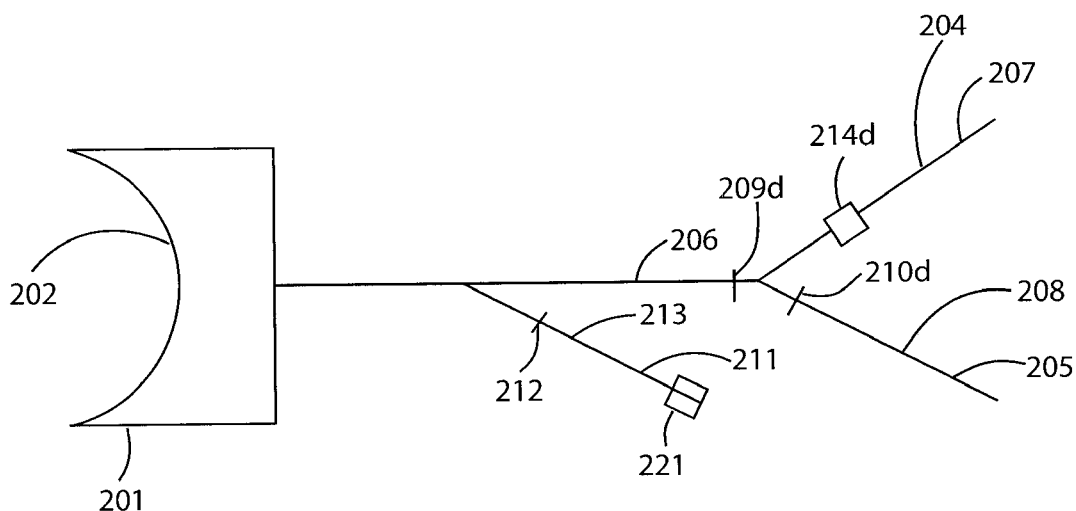

The inlet valves I 209*a-e* and II 210*a-e* are placed in inlet flow lines 204,205 at a position upstream of the common inlet/outlet part 203, common space, with
 a) both inlet valves 209*a*,210*a* being present in the common inlet part 20 (FIG. 2*a*),
 b) each inlet valves 209*b*,210*b* being present in a non-coinciding part 207 and 208, respectively, with one inlet valve per inlet flow line 204,205 (FIG. 2*b*), or
 c) one 209*c* (210*c* not shown) being placed in the common inlet part 206 (i.e. upstream of the common inlet/outlet part 203, =common space, and the other one 210*c* (209*c* not shown) in a non-coinciding part 208 (208 not shown) of one of the inlet flow lines 205 (204 not shown) (FIG. 2*c*).

The sub-pressure resistance for opening may differ between inlet valves placed in different inlet flow lines (see below). If both valves 209*a*,210*a* are placed in the common inlet part 206 they are preferably coinciding with each other (=one single valve) and/or defines a common valve function 209*a*+210*a* that can be opened or closed simultaneously.

The switching means typically comprises a blocking function 214*a-e*,215*a-e* which is placed in the non-coinciding part 207,208 of either one or both of the inlet flow lines 204,205, i.e. upstream of the common inlet part 206 of the inlet flow lines 204,205. This kind of function is capable of switching between blocking (stop flow) and unblocking (permit flow) the non-coinciding part 207,208 of the inlet flow line 204,205 in which the function is placed. The blocking function is independent from the patient's breathing. It thus blocks an inlet valve's responsiveness for inhaling/exhaling when switched to the blocking position and opens for the responsiveness when switched to the unblocking position. Switching between blocking and unblocking is according to the patient's immediate need of gas I or gas II as exercised via the switching means. It means that gas II cannot enter through inlet flow line II 205 when gas I is permitted to enter via inlet flow line I 204 and vice versa when the blocking function is switched to block gas I from entering via inlet flow line I 204. Preferred variants comprises that the blocking function 214*a-e* is present at least in inlet flow line I 204.

The position for a blocking function 214*a-e*,215*a-e* within the non-coinciding part 207,208 of an inlet flow line 204,205 may be upstream, downstream or at the position of the inlet valve 204,205 (if the inlet valve is present). Preference is for upstream. The term "at the position of the valve" includes that an inlet valve 204*a-e*,205*a-e* as such can be switched on and off between being sensitive and being insensitive to sub-pressure by the use of the switching means.

A first variant (FIG. 2*a*) comprises that that the inlet valves 209*a*,210*a* are present as a common valve function 209*a*+210*a* which is placed in the common inlet part 206 upstream of the common inlet/outlet part 203, =common space, combined with a blocking function 214*a* or 215*a* in the non-coinciding part 207,208 of each of the inlet flow lines 204,205. Common valve function in this context comprises a single inlet valve which is common for both inlet flow lines.

A second variant (FIG. 2*b*) comprises that the non-coinciding part 207,208 of each inlet flow line 204,205 comprises a blocking function 214*b*,215*b* and an inlet valve 209*b*,210*b*.

A third variant (FIG. 2*c*) comprises that the non-coinciding part 207,208 of each inlet flow line comprises an inlet valve 209*a*,210*a* but only one of them contains a blocking function 214*c* (215*c* not shown). The sub-pressure resistance of the inlet valve 209*c* of the flow line 204 containing the blocking function 214*c* is then preferably lower than the sub-pressure resistance of the inlet valve of the other inlet flow line. The blocking function is in this variant preferably placed in flow line I 204, i.e. in the inlet flow line for gas I containing nitrous oxide. The sub-pressure resistance of the inlet valve 209*c*,210*c* of the flow line 204*c*,205*c* containing the blocking function is typically lower than the sub-pressure resistance of the inlet valve of the other inlet flow line.

A fourth variant (FIG. 2*d*) comprises an inlet valve 209*d* (210*d* not shown) in the common part 206 of the inlet flow lines 204,205 (upstream of the common inlet/outlet part 203) and one inlet valve 210*d* (209*d* not shown) in the non-coinciding part 208 (207 not shown) of one of the inlet flow lines 205 (204 not shown). The blocking function 215*d* (214*d* not shown) is present in the non-coinciding part 207 (208 not shown) which does not contain an inlet valve, preferably in the non-coinciding part 207 of inlet flow line I 204*d* for gas I which contains nitrous oxide (preferred variant not shown). The inlet valve 209*d* in the common inlet part 206 preferably has a lower sub-pressure resistance than the inlet valve 210*d* placed in a non-coinciding part 208. An additional blocking function (not shown) may also be present in the non-coinciding part of the inlet flow line which has an inlet valve in its non-coinciding part.

It is generally preferred to place a blocking function 214 at least in inlet flow line I 204 for gas I with further preference for having the blocking function 215 also in inlet flow line II 205 for gas II (i.e. in both of the inlet flow lines).

Figure 2E:
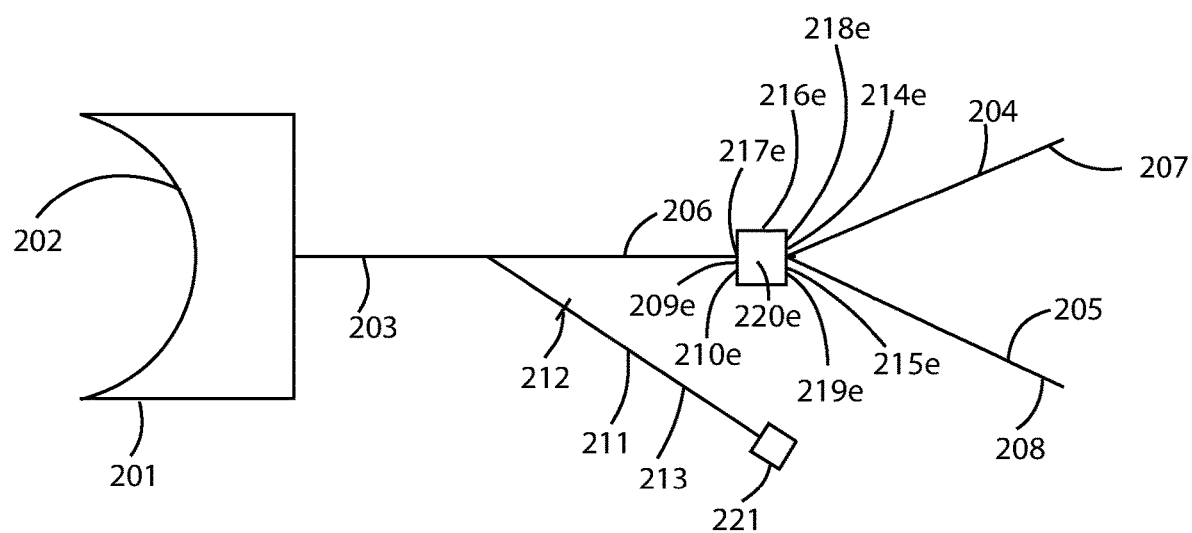
Figure 2F:
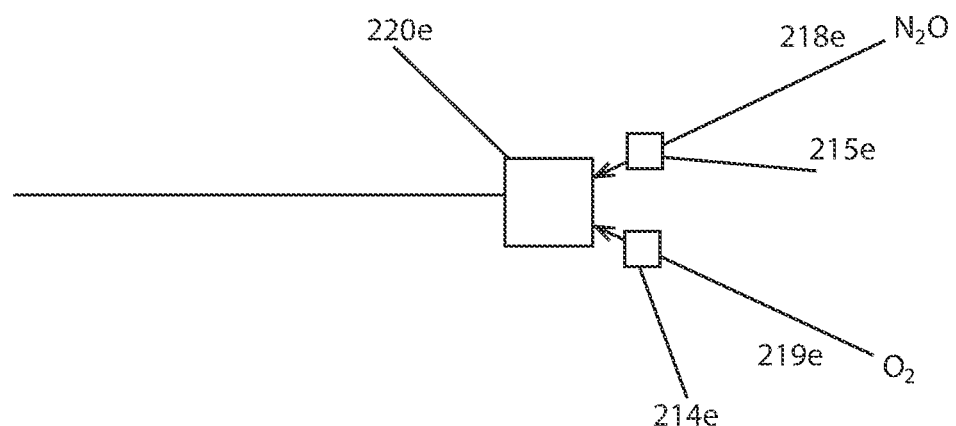

FIG. 2*e* illustrates that the blocking/unblocking function may be part of a mixing arrangement 216*e* for mixing gas containing nitrous oxide with gas containing oxygen but no nitrous oxide (also called diluting arrangement). The concentration of nitrous oxide entering the mixing arrangement is too high for inhaling for the medical treatment to be carried out on the patient. Dilution is required. The gas containing nitrous oxide may for instance derive from a storage tube containing pressurized pure nitrous oxide or prediluted such gas. Gas containing oxygen but no nitrous oxide is of the same type as discussed above. This kind of mixing arrangement comprises,
 i) An outlet 217*e* for gases mixed in the arrangement. The outlet comprises the upstream end of the common inlet part 206 of the inlet flow lines I and II 204,205.
 ii) Two inlets 218*e*,219*e* for gases to be mixed, i.e. one inlet 218*e* for gas containing nitrous oxide and one inlet 219*e* for gas containing oxygen but no nitrous oxide. The inlets comprise the downstream ends of the non-coinciding parts 207,208 of inlet flow lines I 204 and II 205, respectively.
 iii) A mixing zone 220*e* between the two inlets and the outlet. The details of the mixing zone 220*e* are shown in FIG. 2*f*
 iv) A gas regulation function for mixing the two gases in proportions from zero percent nitrous oxide and upwards and at flow rates permitting the mixed gas leaving the mixing arrangement through its outlet to be administered to the individual via the breathing interface of the face mask arrangement. This function may comprise parts that are upstream of the inlets 218e, 219e.

Upwards with respect to concentration typically means an upper limit of at most 70%, such as at most 50% or 40% (v/v), for nitrous oxide.

The blocking function(s) 214e,215e is/are placed upstream of the mixing zone 220e with inlet valves I 209e and II 210e placed upstream and/or downstream of the mixing zone 220e as generally discussed in the foregoing paragraphs.

The positions for inlet and outlet valves and blocking functions should be selected such that gas remaining in the arrangement in downstream parts after a breath and needed to be inhaled in the next breath should be as low as possible.

The blocking function 214,215 of an inlet flow line is preferably placed as close as possible to the downstream end of the non-coinciding part 207,208 in which it is placed. This typically means that the distance between a) a blocking function 214,215 and the breathing interface 202, and/or b) a blocking function 214,215 and the branching off of the non-coinciding part 213 of outlet flow line 211 from the common inlet part 206 typically is ≤about 2 m such as ≤1 m or ≤0.5 m or ≤0.25 m (length of flow line between these two positions).

The inlet valve 209,210 of an inlet flow line 204,205 is preferably placed as close as possible to a) the downstream end of the common inlet part 206 but always upstream of the common inlet/outlet part 203, =common space, with the provisos that when an inlet valve is present in
a) a non-coinciding part 207,208 the preferred positions are as close as possible to the common inlet part 206, and
b) the common inlet part 206 the preferred positions are as close as possible to the common inlet/outlet part 203, =common space.

This typically means that the distance between a) an inlet valve 209,210 and the breathing interface 202, or b) an inlet valve 209,210 and the branching off of the outlet flow line 211 from the common inlet part 203 typically is ≤about 2 m such as ≤1 m or ≤0.5 m or ≤0.25 m (length of flow line between the valve and the interface/branching).

The outlet valve 212 of the outlet flow line 211 is present at a position which is as close as possible to the breathing interface 202 or to the branching off of the non-coinciding part 213 of outlet flow line 211 from the common inlet/outlet part 203 with the proviso that it always is placed within a non-coinciding part 213 of the outlet flow line 211. This typically means a distance of ≤about 0.25 m such as ≤0.15 m (length of outlet flow line between the outlet valve and breathing interface and/or the branching).

The switching means comprises, preferably manual or automatic means, for switching between inlet of gas through inlet flow line I (for gas I) and inlet flow line II (for gas II).

Manually operated comprises that the switching means comprises a button, handle and the like which is preferably placed within about one arm length's distance from the breathing interface of the face mask including on the face mask. Typical distances enables for a patient breathing through the face mask to decide for himself about inlet of gas through inlet flow line or through inlet flow line II according to his need for gas containing nitrous oxide and gas devoid of nitrous oxide. Typical distances comprise ≤50 cm, such as ≤30 cm or ≤15 cm or ≤10 cm with a lower limit being e.g. 5 cm.

Automatic switching means typically comprises that the means has the capability of a) being connected to a sensor for measuring a physiological parameter of a patient which is breathing (inhaling/exhaling) via the inventive arrangement, and
b) using a value obtained by said sensor for i) determining the patient's need for inhaling gas containing nitrous oxide or gas devoid of nitrous oxide, and ii) automatically switching between the gases if the value is within a preset interval, such as above or below a preset limit value.

The parameter used is selected from those that reflect a patient's need for gas containing nitrous oxide or gas devoid of nitrous oxide. This kind of parameters can be found amongst blood pressure, pulse, inhalation/exhalation frequency etc.

The switching means may comprise a resilient portion that allow for a compressed position for inhalation of one of the two gases and a released position for inhalation of the other one of the gases. This kind of means possibly comprises a locking function locking the means at one of the positions, preferably in a releasable way. Resilient portion comprises that the means is spring-loaded, cushion loaded etc.

The switching means comprises that the communication between the means for exercising blocking/unblocking is communicating with the blocking function mechanically and/or by wire or wire-less and/or via electric or electromagnetic signals. The switching means may be battery driven.

The outlet flow line 211 is preferably associated with a sensor 221 for measuring the level of nitrous oxide at a position downstream of the common inlet/outlet part. The preferred measuring position is downstream of the outlet valve 212. The term "associated with" in this context means that the sensor is placed either within the outlet flow line as indicated for the measuring or in the inlet flow line of an apparatus for removing nitrous oxide from exhalation air. This sensor is preferably connected to an alarm function alerting the patient when the level of nitrous oxide in exhalation air is sufficiently low for the face mask to be removed from the patient's face, in other words after the patient has switched from inhaling gas I to gas II and has ventilated out nitrous oxide in blood and lungs via breathing of gas II. The face mask may be removed when the level of nitrous oxide in exhalation air is within an interval of about 20.000-50.000 ppm, preferably 5.000-20.000 ppm, more preferably 1.000-5.000 ppm, and most preferably 100-1000 ppm. This alarm function may be time controlled and is preferably provided as a light signal within the face mask or at a place easily monitored by the patient and possibly alone or together with a sound signal. The light signal may be a green signal, for instance, indicating that the face mask can be removed and a red signal, for instance, indication that the patient still has to exhale through the mask.

The arrangement may also comprise a second outlet flow line for inhalation and exhalation air leaking from the breathing interface during breathing via the mask or during periods when the patient is breathing ambient atmosphere. This normally happens when the mask is affixed to a face or when released from the face during periods when the patient does not need gas containing nitrous oxide. The inlet end of this second outlet flow line is typically circumferential about the inlet parts of the first outlet flow line and the outlet part(s) of the inlet flow line I and inlet flow line II (if present), i.e. the end of the common inlet/outlet part which is next to the breathing interface. The second outlet flow line is typically merging with the first outlet flow line at a position downstream of the outlet valve. Face masks of this kind are called double masks and are descried in for instance WO1982001999 (Lindkvist).

By providing the face mask arrangement according to the first aspect of the invention it is possible to reduce the volume of gas evacuated per hour, and thus the volumetric flow rate of the gas evacuated, by known face masks from about 25 m³/h to about 2.5 m³/h or even to about 1.8 m³/h, thus a reduction by a factor 10. In so doing, it is possible to reduce the sound produced by the arrangement, the energy required by the equipment, and the costs for and the volume of the equipment for decomposition of nitrous oxide may thus be reduced significantly.

More particularly, by providing the face mask arrangement with a switching means enabling a patient to switching between inhalation through inlet flow line I and inlet flow line II, depending on the patient's immediate need of gas I or gas II, it is possible to reduce speed of flow of the gas evacuated by the face mask. This reduction of the speed of flow is possible due to the fact that the patient does not need to remove the mask from his face when gas containing nitrous oxide is not needed.

Apparatus for the Removal of Nitrous Oxide From Exhalation Air

Figure 3:
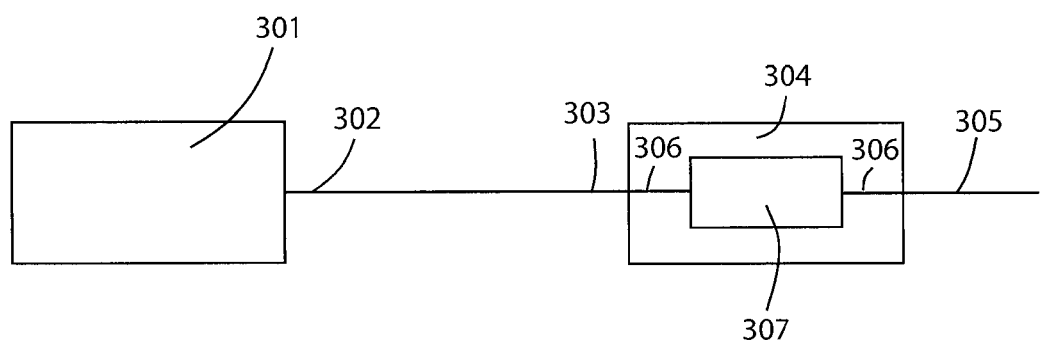
FIG. 3 illustrates a preferred variant in which the inventive arrangement is part of a system comprising also an apparatus for the removal of nitrous oxide from exhalation air collected by the use of the arrangement.

FIG. 3 illustrates a preferred variant of the invention in which an inventive face mask arrangement 301 as described above is part of a system which further comprises an apparatus 304 for removing nitrous oxide from exhalation air deriving from a patient inhaling gas containing nitrous oxide. This apparatus comprises i) a main flow line 306 with an inlet 303 and an outlet 305 and there between a through-flow removal chamber 307 which is capable of removing nitrous oxide present in exhalation air, which removal chamber is
  a) a decomposition chamber $307_{deco}$ capable of decomposing nitrous oxide to nitrogen and oxygen, preferably at exothermic conditions and/or preferably catalytically, or
  b) an adsorption chamber $307_{adso}$ which is capable of adsorbing nitrous oxide (also called adsorption unit), and
ii) is connected via its inlet 303 to the outlet end of the outlet flow line 302 of the arrangement 301.

The apparatus is adapted to the fact that the level of nitrous oxide at the outlet end of the outlet flow line of the face mask arrangement of the invention typically reaches peak levels which are ≥0.5%, such as ≥1% or ≥2% or ≥5% or ≥10%, and ≤70%, such as ≤50%, when the arrangement is connected to a patient breathing gas containing nitrous oxide. The flow velocity at the outlet end is typically ≤3.5 m³ per hour.

Apparatus Which Contains a Decomposition Chamber

The apparatus is further characterized by comprising
a) a catalyst material which is placed in the decomposition chamber and capable of decomposing nitrous oxide to nitrogen and oxygen, preferably under exothermic conditions, and
b) a heat controlling arrangement comprising at least one of
  i) a regulatable air diluting function for varying (decreasing or increasing) the concentration of incoming gas containing nitrous oxide with air in response to the temperature in the removal chamber during the decomposition and/or in response to the concentration of nitrous oxide in incoming gas containing nitrous oxide in order to control (e.g. change=decrease or increase) heat evolution during the decomposition, and/or
  ii) a heat-neutralizing medium placed within the removal chamber in intimate heat transfer contact with a catalyst material, and/or
  iii) a conventional heater for preheating gas containing nitrous oxide which is entering a removal chamber in the form of a decomposition chamber and/or
  iv) a conventional heat exchanger for cooling gas leaving the removal chamber and heating incoming gas, and/or
  v) a regenerative heat exchanger based on a reversible fixed heat absorbent for cooling gas leaving the removal chamber and heating incoming gas.

Preferred apparatuses containing a decomposition chamber comprises as heat controlling functions at least one of (i), (ii) and (iii) in combination with (iv) and/or (v), with further preference as they are defined in this specification. See further the patents and patent applications discussed below.

Catalyst Material

Suitable catalyst materials may be found amongst those that are effective for decomposing nitrous oxide into $N_2$ and $O_2$ at a temperature that typically should be within the interval of 200-900° C., such as within 350-900° C. See for instance WO2010071538 (Nordic Gas Cleaning AB), WO2002068117 (US20030181324, Showa Denko), WO 2002026355 (Showa Denko KK), US20100166632 (Stichting Energieonderzoek Centrum Nederland), US2009136403 (W.C. Hereaus), references cited in this publications and many others. The catalyst material typically is in the form particles packed to a porous bed in the decomposition chamber.

Suitable catalyst materials shall give only trace levels of nitrous oxide in gas exiting the decomposition chamber. Trace levels in this context means that the levels of nitrous oxide are ≤4000 ppm, such as ≤1000 ppm or ≤500 ppm in gas leaving the decomposition chamber and/or that the level of nitrous oxide in gas leaving the decomposition chamber relative to its level in gas entering the chamber is ≤10% or ≤5% or ≤1%.

Suitable catalyst materials shall also give trace levels of nitrogen oxides ($NO_x$) other than nitrous oxide in gas leaving the decomposition chamber. This primarily refers to ≤2 ppm, such as ≤1 ppm or ≤0.5 ppm or ≤0.1 ppm or ≤0.05 ppm.

The preferred catalyst material is as outlined in WO 2010071538 (Nordic Gas Cleaning AB) and typically comprises a catalytically active metal oxide containing either one or both of copper oxide and manganese oxide, and/or a support material which preferably is in the form of particles and/or typically is based on alumina. The amount of the catalytically active metal oxide is typically in the range of 5-30% with preference for 11-17% (by weight).

There may be even larger benefits with catalyst material specifically dedicated for the decomposition of nitrous oxide. This includes catalyst material containing other metals than those specifically preferred according to the preceding paragraph. Such other metals may be selected from palladium and/or rhodium and many others as outlined in e.g. WO 2002026355 (Showa Denko KK), WO2005110582 (Stichting Energieonderzoek Centrum Nederland), US2009136403 (W.C. Hereaus). This also includes catalyst material having optimal working efficiency at the lower part of the temperature interval given above. See in particular US2009136403 (W.C. Hereaus).

Diluting Function

The diluting function may be as outlined in EP 2165756 (Linde AG) and/or international patent application PCT/SE2012/000044 (U.S. Ser. No. 61/4693, Nordic Gas Cleaning AB). The diluting function is typically used to control heat evolution during exothermic decomposition taking place within the decomposition chamber. This may be particularly beneficial when decomposing nitrous oxide close-to the patient meaning higher concentrations of nitrous oxide promoting exothermic conditions for the decomposition ($\geq$1-2% v/v). The diluting function is typically placed at the inlet of the apparatus and typically comprises an inlet flow line for diluting air. This inlet flow line typically comprises a valve enabling gradual opening and gradual closing for varying the inlet of diluting air and consequently also the dilution and concentration of nitrous oxide. This valve may alternatively be a stop-flow valve. The diluting function preferably is associated with a) a sensor arrangement for measuring a flow parameter (e.g. flow velocity) and/or the level of nitrous oxide at the inlet and/or the temperature in the decomposition chamber/catalyst material, and/or
b) a flow creating function, such as a blower, which can be used for changing the flow velocity through the decomposition chamber and/or in the inlet flow line for diluting air.

The diluting function should be capable of varying the dilution of incoming gas containing nitrous oxide around a preset value which typically is within the interval of 1:1 to 1:50. The preferred concentrations of nitrous oxide which enters the decomposition chamber should be within the lower part of the exothermic concentration range, e.g. concentrations within the interval of from about 1-2% with upper limits such as about 10%, 15%, 25%, 40% or 50% (v/v). During operation the valve in the inlet for diluting air, if present, may be set to a predetermined value, e.g. fully or partly opened, and/or the flow creating function to a predetermined flow velocity. One or both of these two parameters may then be changed in response to values measured by sensors placed along the flow line passing through the decomposition chamber.

Heat-Neutralizing Medium Within the Decomposition Chamber

The use of a heat-neutralizing medium placed within the removal chamber in intimate heat transfer contact with a catalyst material is described i.a. in international patent application PCT/SE2012/000044 (U.S. 61/469,381, Nordic Gas Cleaning AB). The term "intimate" in this context in particular includes that the contact supports maintenance of the temperature in the decomposition chamber at an acceptable level, which in turn depends on the stability of the catalyst material, the heat neutralizing media, the material from which the chamber is manufactured etc and also variables such as effective working temperature range for the catalyst material.

The heat neutralizing medium in the decomposition chamber is typically a heat absorber.

There are mainly two different kinds of heat absorbers that can be used:

a) fixed heat absorbents (also called heat buffers) which are capable of retaining absorbed heat, e.g. in the form of a porous monolith or more preferably particles, and
b) heat absorbers in the form of conduits through which a cooling fluid is passing for removing heat taken up by the fluid via the walls of the conduits (fluid=gas or liquid) (not shown).

In one embodiment, in the decomposition chamber, intimate heat transfer contact between the catalyst material and the heat neutralizing medium can be strengthened by arranging so that the catalyst material and the heat neutralizing medium are mutually embracing each other. In other words the heat neutralizing medium should extend into and/or surround the catalyst material to minimize local areas of heat excess that would cause the decomposition reaction to run out of control within such areas and subsequently also throughout the chamber. Heat neutralizing media which are present in the decomposition chamber should thus surround the catalyst material, and may for instance be more abundant in one or more zones or segments compared to bordering and/or more or less evenly distributed in the volume occupied by the catalyst material.

In another embodiment, in the decomposition chamber, the catalyst material and the heat neutralizing medium can be provided in alternately layers which are in intimate heat transfer contact with each other.

Acceptable heat absorption materials can be selected from materials that are in the form of particles and have heat capacities $\geq$0.1 kJ/kg and K with preference for those of higher heat capacities, such as $\geq$0.4 kJ/kg and K, or $\geq$0.8 kJ/kg and K. An upper limit is typically $\leq$10 kJ/kg and K.

The catalyst material and the heat neutralizing medium in the form of a fixed heat absorbing material are in preferred variants essentially homogenously distributed in relation to each other within one or more zones of the chamber. If both the heat absorbing material and the catalyst material are in the form of particles, the two materials are preferably mixed with each other to form a porous bed (=a catalyst/heat absorbing zone).

Heating of Gas Entering the Decomposition Chamber

The conventional heater, e.g. an electrical heater, associated with the decomposition chamber is typically placed within the chamber upstream of the catalytic material. The heater is preferably gradually adjustable, e.g. stepwise or continuously, within a certain effect range starting from 0 W and with maximal effect $\geq$0.5 kW, such as $\geq$1 kW or $\geq$1.5 kW. The typical upper limit is 2 kW or 5 kW. Other heating principles may also be suitable, e.g. microwave heating.

Conventional Heat Exchangers

The conventional heat exchanger of the apparatus may be a shell and tubular heat exchanger, a plate heat exchanger etc.

Regenerative Heat Exchanger

A regenerative heat exchanger as applied to decomposition of nitrous oxide in a catalytic bed comprises a heat absorber in which heat in the hot gas exiting a decomposition chamber is first transferred and stored in the heat absorber from which heat subsequently is transferred to incoming gas that is about to enter the decomposition chamber. The catalyst bed in the decomposition chamber may be segmented with each segment being separated from the other segments by a zone devoid of catalytic material. The heat absorber is divided into different parts with each part being in heat transfer contact with gas entering/exiting each segment (WO 2011075033 (Nordic Gas cleaning AB), US 20110262332 (Nordic Gas Cleaning AB) and US2010032283 (Sumitomo)). The heat absorbent material is of the same kind as described above for (ii), i.e. the heat absorbent material of the fixed heat adsorbent which can be placed in the decomposition chamber.

Apparatus Which Contains an Adsorption Unit

In a second variant the removal chamber is part of an adsorption unit. The removal chamber contains a nitrous oxide reversible adsorbent as discussed in a WO 2009095601, WO 2009095605 and WO 2009095611 (all of Air Liquid) and PCT/SE2012/000043 (U.S. 61/469,369, Nordic Gas cleaning). The term reversible means that the adsorbent can be regenerated by passing desorbing gas through the adsorbent. The unit has in principle four ports: a) an inlet port for inlet of exhalation air, b) an outlet port for discharging exhalation air processed in the chamber, c) an inlet port for inlet of desorbing gas, and b) an outlet port for discharging desorbing gas from the adsorbent.

The ports preferably coincide:
i) port a) with port c) or port d) and/or
ii) port b) with port c) or d) with preference for "and"

The adsorption unit preferably has at least one of
a) a heating function for heating the adsorbent during desorption,
b) one or more flow changing functions, preferably a blower, for changing the flow through the adsorption unit during adsorption or during desorption, and/or
c) one or more sensors capable of measuring amounts of nitrous oxide on the adsorbent during or after adsorption and/or desorption.

Heating Function

The heating function shall be capable of heating a through-passing desorbing gas and/or the adsorbent to a temperature enabling efficient release of nitrous oxide from the adsorbent during desorption. Suitable temperatures depend on the desorbing gas, adsorbent material etc, and are typically found in the interval of ≤400° C., such as 100-400° C. or 100-250° C. The effect of the heating function at least for preheating should be within the interval of 150-2500 W with preference for within 200-500 W. The heater may be gradually adjustable with respect to effect. It is preferably in the form of an electrical heating element possibly supported by a heat exchanger transferring heat in gas exiting the adsorbent to incoming cold desorbing gas.

Flow Changing Functions

A flow changing function, preferably a blower, placed on the adsorption unit may be used during adsorption for securing subpressure and hinder leakage of nitrous oxide at positions upstream of the adsorption unit. The preferred position is upstream of the heating function (if present), i.e. also upstream of the adsorbent (upstream refers to adsorption flow). This kind of flow changing function is capable of being turned off during desorption and turned on during adsorption. It is preferably battery-driven.

Sensors

A sensor used for determining amount of nitrous oxide on the adsorbent may be based on changes in weight of the adsorbent/unit, changes in available and/or utilized capacity and/or other parameters changing as a consequence of adsorption and/or desorption, e.g. the position of the adsorption front during on-going adsorption, changes in level of nitrous oxide in the adsorption or desorption low downstream of the adsorbent, changes in temperature in the adsorbent due to evolution of heat during adsorption etc. Thus a typical sensor may be a weight sensor, such as a load cell, a spectrometric sensor, a temperature sensor etc.

System Containing the Face Mask Arrangement ($2^{ND}$ Aspect of the Invention)

The system has as the characterizing feature that it comprises both the face mask arrangement of the first aspect and the apparatus for removal as defined above as an optional feature of the first aspect. The aspect is adapted to close-to patient use for collecting inhalation air from patients inhaling gas containing nitrous oxide and subsequently removing the nitrous oxide from the collected inhalation air during the collection from and administration to the patient of gas containing nitrous oxide.

Use of the Face Mask Arrangement for Administration of Nitrous Oxide to a Patient Via Inhalation and/or Collection and Removing Nitrous Oxide From Exhaled Air of a Patient During Administration ($3^{Rd}$ Aspect).

The invention relates also to the use of the face mask arrangement according to the $1^{st}$ aspect of the invention for administration of nitrous oxide to a patient via inhalation and/or collecting and removing nitrous oxide from exhaled air of a patient during the administration.

The invention claimed is:

1. A face mask arrangement for alternately administering a gas I containing nitrous oxide and a gas II devoid of nitrous oxide to a patient via inhalation, comprising:
    a) a face mask having a breathing interface,
    b) first and second inlet flow lines for the gas I and the gas II, respectively, for supplying the gas I and the gas II to the breathing interface, and
    c) an outlet flow line for evacuation of exhaled gas from the breathing interface, wherein:
    d) the first and second inlet flow lines merge into a common inlet part which terminates in the breathing interface, and
    e) a downstream part of the common inlet part coincides with an upstream part of the outlet flow line, forming a common inlet/outlet part,
    f) each of the first and second inlet flow lines comprises an inlet valve, each inlet valve being capable of opening in response to inhalation, and being capable of closing in response to exhalation,
    wherein said face mask arrangement comprises a switching means for switching between inhalation through the first inlet flow line and the second inlet flow line, said switching means being configured to be activated by the patient in response to the patient's immediate need of the gas I or the gas II and enabling blocking/unblocking, of the first and second inlet flow lines depending on the patient's immediate need of the gas I or the gas II,
    wherein:
    a) the respective inlet valves are present in a non-coinciding part of each of said first and second inlet flow lines,
    b) a blocking function is present only in one of the first and second inlet flow lines, and
    c) the inlet valve which is placed in the non-coinciding part of the inlet flow line which is lacking blocking function has a sub-pressure resistance that is higher than the other inlet valve, and
        wherein said face mask arrangement further comprises an alarm function indicating when the level of nitrous oxide in exhalation air is below a predetermined value so that the face mask may be removed from the patient's face.

2. The arrangement according to claim 1, wherein the blocking function is present upstream of the inlet valve of the non-coinciding part of the inlet flow line which includes the blocking function.

3. The arrangement according to claim 1, wherein the length of flow line between the blocking function and the breathing interface of the face mask is at most 2 meters.

4. The arrangement according to claim 1, wherein said switching means comprises a manual means or an automatic means for switching between the inhalation of gas through the first and the second inlet flow lines.

5. The arrangement according to claim 4, wherein said switching means is configured to be operated by the patient, and is located within 40 cm from the breathing interface of the face mask.

6. The arrangement according to claim 4, wherein said switching means is resilient with a compressed position for inhalation of one of the gas I or the gas II and a released position for inhalation of the other one of the gas I or the gas II.

7. The arrangement according to claim 1, wherein the switching means is battery-driven, with communication between said switching means and said blocking function being by wire or wireless.

8. The arrangement according to claim 1, wherein the alarm function is configured to be activated as a response to a sensor detecting the level of nitrous oxide in exhalation air.

9. The arrangement according to claim 1, wherein the alarm function is a light signal and/or a sound signal.

10. The arrangement according to claim 1, wherein the face mask may be removed when the level of nitrous oxide in exhalation air is within a predetermined value of 100-1000 ppm.

11. A system for collecting nitrous oxide including the arrangement of claim 1, wherein the system further comprises an apparatus which:
   i) is adapted for removing nitrous oxide present in a flow exiting through an outlet end of the outlet flow line at a level which is ≥0.5%, and at a flow velocity of ≤3.5 $m^3$ per hour, by
      a) decomposing nitrous oxide into nitrogen and oxygen or
      b) adsorption, and
   ii) is connected to the outlet end of the outlet flow line.

12. The arrangement according to claim 2, wherein said apparatus comprises:
   a) a removal chamber containing a catalyst material which is capable of decomposing nitrous oxide to nitrogen and oxygen,
   b) a heat controlling arrangement comprising at least one of:
      i) a regulatable air-diluting function for increasing/decreasing the dilution of incoming gas containing nitrous oxide with air in response to a temperature in the removal chamber during the decomposition, and/or
      ii) a heat-neutralizing function placed within the removal chamber in intimate heat transfer contact with the catalyst material, and/or
      iii) a heater for preheating incoming inhalation air, and/or
      iv) a conventional heat exchanger, and/or
      v) a regenerative heat exchanger.

13. The arrangement according to claim 2, wherein said apparatus comprises:
   a) a removal chamber which contains a nitrous oxide reversible adsorbent, and
   b) at least one of:
      i) a heating function for heating the adsorbent during desorption,
      ii) a blower for changing flow and/or hinder leakage of nitrous oxide during adsorption, and/or
      iii) one or more sensors capable of measuring amounts of nitrous oxide on the adsorbent during or after adsorption and/or desorption.

14. A system comprising the face mask arrangement according to claim 1 and an apparatus for collecting inhalation air from patients inhaling gas containing nitrous oxide and subsequently removing the nitrous oxide from the collected inhalation air during the collection from and administration to the patient of gas containing nitrous oxide.

15. A method comprising administering nitrous oxide to a patient via inhalation and collecting nitrous oxide from exhaled air of a patient using the face mask arrangement of claim 1.

* * * * *